United States Patent
Brunk

[11] Patent Number: 5,916,429
[45] Date of Patent: Jun. 29, 1999

[54] DIRECT BLOT ELECTROPHORESIS APPARATUS AND METHOD

[75] Inventor: Donald Harvey Brunk, Wilmington, Del.

[73] Assignee: Qualicon Inc., Wilmington, Del.

[21] Appl. No.: 08/904,361

[22] Filed: Aug. 1, 1997

[51] Int. Cl.$^6$ .......................... G01N 27/26; G01N 27/447
[52] U.S. Cl. ............................................ 204/614; 204/464
[58] Field of Search ...................................... 204/614, 464

[56] References Cited

U.S. PATENT DOCUMENTS

| | | | |
|---|---|---|---|
| 4,075,069 | 2/1978 | Shinohara et al. | 205/560 |
| 4,622,124 | 11/1986 | Kreishev et al. | 204/614 |
| 4,631,120 | 12/1986 | Pohl | 204/465 |
| 4,631,122 | 12/1986 | Pohl | 204/614 |
| 4,632,901 | 12/1986 | Valkirs et al. | 435/5 |
| 4,702,814 | 10/1987 | Audeh | 204/616 |
| 4,994,166 | 2/1991 | Fernwood et al. | 204/614 |
| 4,995,948 | 2/1991 | Poa et al. | 205/47 |
| 5,106,468 | 4/1992 | Chimenti | 204/564 |
| 5,234,559 | 8/1993 | Collier et al. | 204/464 |
| 5,453,174 | 9/1995 | Van Anglen et al. | 205/117 |
| 5,460,705 | 10/1995 | Murphy et al. | 204/252 |
| 5,662,789 | 9/1997 | MacDougell et al. | 205/688 |

Primary Examiner—William H. Beisner
Assistant Examiner—John S. Starsiak, Jr.

[57] ABSTRACT

In a horizontal gel, direct blot electrophoresis separation apparatus, device to remove gas dissolved in the buffer solution surrounding the anode at a location remote from the interface between the gel and the moving membrane, such as a gas evolution member disposed between the anode and the moving membrane of such apparatus, has been found to result in more consistent and readable blot patterns with less defects.

5 Claims, 2 Drawing Sheets

DIRECT BLOT ELECTROPHORESIS APPARATUS AND METHOD

BACKGROUND OF THE INVENTION

This invention relates to an improvement in a direct blot electrophoresis apparatus and method for performing direct blot electrophoresis.

Electrophoresis is a separation technique wherein fragments of materials (e.g., DNA) are caused to migrate across a gel in response to an electrical current. The rate of migration is proportional to the molecular weight of the fragment, thus resulting in a separation. In direct blot electrophoresis, such as is taught in U.S. Pat. Nos. 4,631,112 and 4,631,120, the fragments are transferred from the edge of the gel to a moving belt.

U.S. Pat. No. 5,234,559 teaches an improvement in direct blot electrophoresis wherein a membrane, stabilized by a frame, is moved substantially orthogonal relative to the plane of the separation gel. The frame moves at a controlled velocity away from a line of contact with the edge of the gel, which results in a controlled tension in the membrane as a function of the loading on the line of contact between the membrane and the gel.

It is known in the art that the blot patterns produced in direct blot electrophoresis apparatus are sometimes defective; that is, are blurred, smeared, or distorted, which limits the usefulness of that data. The present invention is based on the discovery that such defects in the blot patterns are caused by the evolution of dissolved gas bubbles at the gel/membrane interface.

SUMMARY OF THE INVENTION

In one aspect, the invention provides an improved direct blot electrophoresis separation apparatus of the type having a cathode, an anode submerged in a buffer solution, an electrophoresis gel disposed between the anode and the cathode and a membrane moving at a controlled velocity substantially orthogonal to a horizontal plane of the gel, the improvement wherein comprising means for removing gas dissolved in the buffer solution at a location remote from the gel/membrane interface.

In another aspect, the invention provides an improved method for direct blot electrophoresis separations of the type including the steps of loading a sample on an electrophoresis gel, applying an electrical current to the gel to separate the sample into components and cause the components to migrate across the gel, and transferring the components to a membrane moving at a controlled velocity substantially orthogonal to a horizontal plane of the gel, the improvement wherein comprising the step of removing dissolved gas at a location remote from the interface between the gel and the moving membrane.

DETAILED DESCRIPTION

Figure 1:
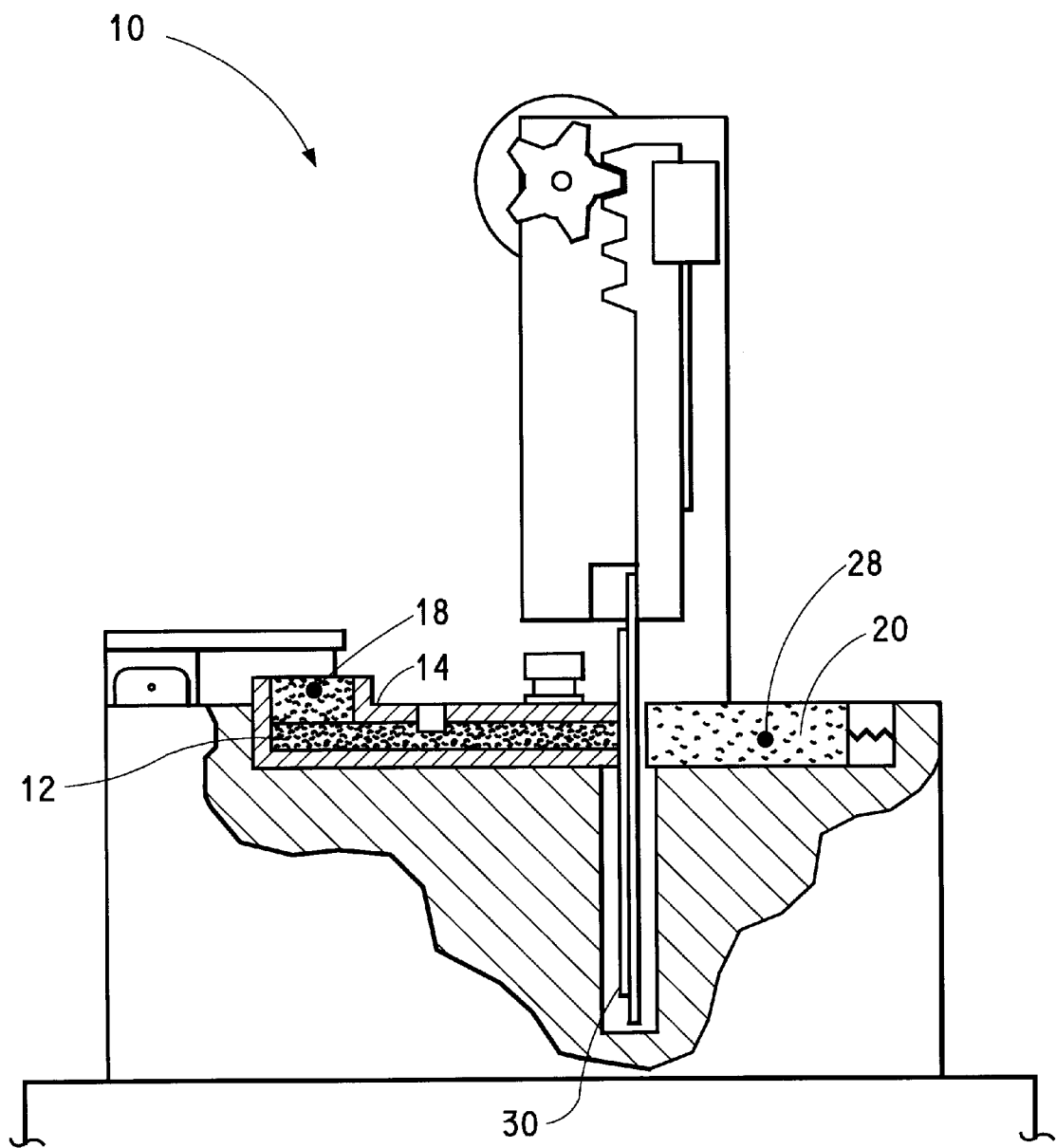
FIG. 1 is a cross-sectional view of a prior art electrophoresis separation apparatus as taught in U.S. Pat. No. 5,234,559.

With reference first being made to FIG. 1, an electrophoresis separation apparatus designated generally at 10 comprises an electrophoresis gel 12 enclosed in a frame 14. The frame 14 and gel 12 together comprise a disposable cassette that is replaced for each test in practice. The electrophoresis separation apparatus illustrated in FIG. 1 is disclosed in detail in U.S. Pat. No. 5,234,559, the disclosure of which is incorporated herein by reference.

Once a sample material (e.g., nucleic acid) is loaded onto the gel 12, an electrical current is applied to the gel via cathode 18 and anode 28. The current causes the sample material to migrate toward anode 28. The rate of migration of the components comprising the sample is proportional to the molecular weight of the components, thus resulting in a separation of those components in the gel. When the components of the sample material reach the edge of gel 12, they are transferred onto the membrane 30, which is moving in a controlled velocity as is known in the art.

As noted, the present invention is based on the discovery that gas bubbles can sometimes form at the interface between the gel 12 and the moving membrane 30. The presence of these gas bubbles can lead to interference with the transfer of material from the gel to the membrane, which in turn causes defects in the resulting blot pattern. During electrophoresis, oxygen is generated at the anode 28 and is dissolved in the buffer medium 20. This is particularly true for anodes comprising a 1.5 mm diameter platinum-coated titanium rod. In the prior art apparatus and method, a substantial portion of the dissolved oxygen evolves from the buffer medium 20 near the interface between membrane 30 and gel 12, which causes the aforementioned defects in the direct blot patterns.

Figure 2:
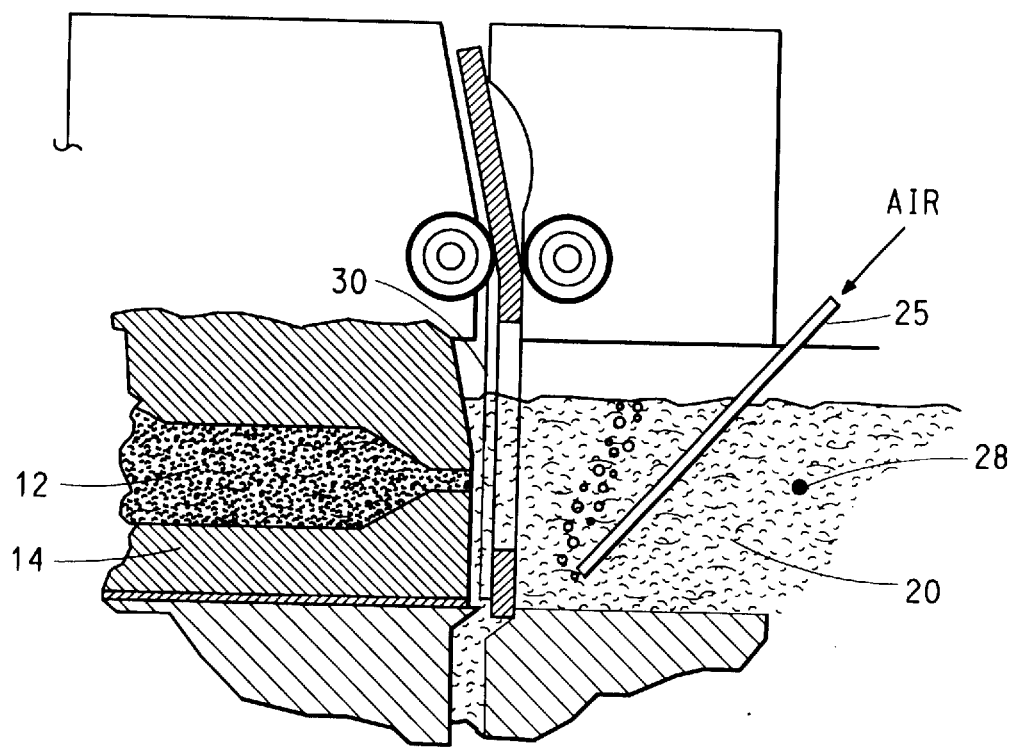
FIG. 2 is an enlarged cross-sectional view of the transfer region between the gel and the membrane in a direct blot electrophoresis apparatus incorporating an oxygen bubbling device in accordance with one embodiment of the present invention.

In accordance with the present invention, the gas dissolved in the buffer medium surrounding the anode is removed at a location remote from the interface between the gel and the membrane. This may be accomplished in several ways. For example, with reference to FIG. 2, air is bubbled into the buffer medium 20 during electrophoresis via inlet 25. As the air bubbles rise, gas dissolved at the supersaturated concentration level in the buffer medium will tend to come out of solution and join the rising air bubbles. Accordingly, bubbling air into the buffer medium 20 will remove the dissolved gas at or near the anode 28 and remote from the membrane 30.

In another embodiment, a gas evolution member is disposed in the buffer solution to remove the dissolved gas. The gas evolution member can conveniently be disposed around the periphery of the reservoir containing the buffer medium 20 and the anode 28 or can be disposed intermediate the anode and the interface between the gel and the moving membrane. The function of the gas evolution member is to remove the dissolved gas by promoting bubble formation so that the dissolved gas leaves the buffer medium remote from the membrane/gel interface and, most preferably, at or near the anode. The gas evolution member can take the form of a coating on the walls of the reservoir, a web traversing the reservoir, or a structure of any convenient shape (i.e., cylinder, polygonal tube, or the like) disposed either horizontally or vertically within the reservoir. It is particularly preferred that the gas evolution member be placed in close proximity to the anode to improve the efficiency of the member at removing/trapping dissolved gas and encouraging evolution of the gas.

The material used for the gas evolution member should be non-conducting so as not to interfere with the electrical current being applied to the gel during the separation process. In addition, if a web or other structure is used, it should be such as to promote the formation of bubbles, such as a porous mesh or screen material. In a particularly preferred embodiment, the gas evolution member comprises a sheath disposed around the anode.

Figure 3:
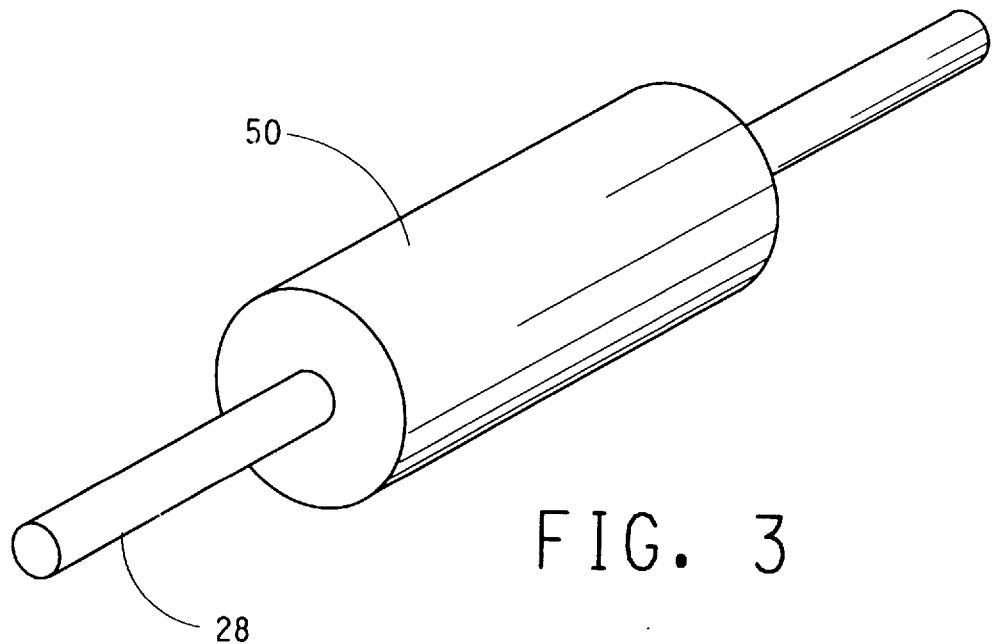
FIG. 3 is an enlarged perspective view of an anode having a porous sheathing in accordance with a preferred embodiment of the present invention.

With particular reference now being made to FIG. 3, the anode 28 is shown having a sheath 50 disposed around the anode 28. The sheath 50 comprises a porous material, such as a nylon cloth screen or mesh. Particularly preferred is an electrically non-conducting, nylon mesh having 250 μm mesh opening and a 62.0 mesh count per inch. Such a mesh is available as QCMN250S from Small Parts, Inc. (Miami Lakes, Fla.).

EXAMPLES

A 76 mm×57 mm piece of QCMN250S was wrapped around a 1.5 mm mandrel to produce a 57 mm×6 mm cylindrical sheath. The sheath was wrapped with heat-resistant adhesive tape made from Kapton® (E. I. du Pont de Nemours & Co.) to maintain its shape. After removing the mandrel, the sheath was heat set at 121° C. for 15 minutes in an autoclave. The heat set sheath was then removed and the ends trimmed of any frayed fibers.

Sheaths formed as above were then installed on the anode in the electrophoresis separation module of four different RiboPrinter® mobil characterization units (Qualicon, Inc., Wilmington, Del.) and on six different stand-alone separation and transfer modules, each of which utilize an electrophoresis apparatus of the type taught in the aforementioned U.S. Pat. No. 5,234,559. A total of 85 blot patterns were then created and the patterns visually inspected and rated for defects. Results are shown in Table 1.

TABLE 1

| Rating | Description | Percent |
|---|---|---|
| 0 | No defects | 75 |
| 1 | Fine streaks, data unaffected | 20 |
| 2 | Medium streaks, data unaffected | 4 |
| 3 | Large streaks, data affected | 1 |
| 4 | Heavy streaks, data affected | 0 |

For comparison purposes, blot patterns were generated on two of the four RiboPrinter® units before and after the sheaths were installed. Results are shown in Table 2.

TABLE 2

| | Unit 1 | | Unit 2 | |
|---|---|---|---|---|
| # of patterns rated | Before 27 | After 10 | Before 30 | After 16 |
| Rating | % | | % | |
| 0 | 7 | 70 | 7 | 69 |
| 1 | 11 | 30 | 40 | 25 |
| 2 | 26 | 0 | 47 | 6 |
| 3 | 19 | 0 | 7 | 0 |
| 4 | 37 | 0 | 0 | 0 |

An additional 18 blot patterns were run on the RiboPrinter® units containing the sheathed anodes and compared against data for the sample material used for quality control purposes. All patterns were within normal range, indicating that the use of the sheathed anode did not affect performance of the RiboPrinter® units.

What is claimed is:

1. In a direct blot electrophoresis separation apparatus of the type having an anode submerged in a buffer solution, an electrophoresis gel and a membrane moving at a controlled velocity substantially orthogonal to a horizontal plane of the gel and in contact therewith, the improvement wherein comprising means for removing gas dissolved in the buffer solution at a location remote from the gel/membrane interface, said means comprising a gas evolution member disposed between the anode and the moving membrane, said gas evolution member comprising a porous sheath disposed around the anode and wherein said sheath comprises a heat set nylon mesh.

2. The apparatus of claim 1, wherein said porous sheath comprises a plurality of wrappings of a nylon mesh having 250 μm mesh opening and a 62.0 mesh count per inch.

3. The apparatus of claim 1, wherein said porous sheath comprises is formed in a cylindrical shape.

4. The apparatus of claim 3, wherein said porous sheath comprises a 57 mm×6 mm cylinder.

5. The apparatus of claim 4, wherein said cylinder has an internal diameter of 1.5 mm.

* * * * *